United States Patent [19]

Causey, III et al.

[11] Patent Number: 5,318,591
[45] Date of Patent: Jun. 7, 1994

[54] IMPLANTABLE CARDIOVERTER-DEFIBRILLATOR HAVING EARLY CHARGING CAPABILITY

[75] Inventors: James D. Causey, III, Simi Valley; Brian M. Mann, Beverly Hills, both of Calif.

[73] Assignee: Siemens Pacesetter, Inc., Sylmar, Calif.

[21] Appl. No.: 980,420

[22] Filed: Nov. 23, 1992

[51] Int. Cl.$^5$ ............................................ A61N 1/00
[52] U.S. Cl. ............................................ 607/5; 607/7
[58] Field of Search ................ 128/419 PT, 419 D

[56] References Cited

U.S. PATENT DOCUMENTS

| | | | |
|---|---|---|---|
| 4,398,536 | 8/1983 | Nappholz et al. | 128/419 |
| 4,427,011 | 1/1984 | Spurrell et al. | 128/419 |
| 4,541,430 | 9/1985 | Elmqvist et al. | 128/419 |
| 4,739,437 | 4/1988 | Morgan | 361/88 |
| 4,774,952 | 10/1988 | Smits | 128/419 |
| 4,809,697 | 3/1989 | Causey, III et al. | 128/419 |
| 4,869,252 | 9/1989 | Gilli | 128/419 D |
| 4,895,151 | 1/1990 | Grevis et al. | 128/419 D |
| 4,940,052 | 7/1990 | Mann et al. | 128/419 |
| 4,944,299 | 7/1990 | Silvian | 128/419 |
| 4,989,602 | 2/1991 | Sholder et al. | 128/419 |
| 4,991,603 | 2/1991 | Cohen et al. | 128/786 |
| 4,998,975 | 3/1991 | Cohen et al. | 128/419 |
| 5,103,822 | 4/1992 | Duncan | 128/419 |
| 5,163,427 | 11/1992 | Keimel | 128/419 D |

Primary Examiner—William E. Kamm
Assistant Examiner—Scott M. Getzow
Attorney, Agent, or Firm—Bryant R. Gold; Lisa P. Weinberg; Leslie S. Miller

[57] ABSTRACT

An implantable cardioverter-defibrillator (ICD) provides a tiered therapy designed to automatically terminate tachyarrhythmias using the least aggressive therapy possible while reducing the "time-to-therapy." The tiered therapy first applies a first tier of therapy (e.g., antitachycardia). If unsuccessful, the tiered therapy next applies a second tier of therapy (e.g., cardioversion pulse with a pulse of moderate energy). If unsuccessful, the tiered therapy finally applies a third tier of therapy (e.g., a high energy pulse). So that more aggressive (higher energy) tiered therapies may be applied as early as possible following the failure of a less aggressive (lower energy) therapy, the ICD begins charging one or more high voltage capacitors of the ICD in parallel with the application of the less aggressive therapy, and/or in parallel with the verification interval immediately following a prior therapy attempt during which the ICD attempts to verify the successful termination of the tachyarrhythmia.

25 Claims, 5 Drawing Sheets

IMPLANTABLE CARDIOVERTER-DEFIBRILLATOR HAVING EARLY CHARGING CAPABILITY

FIELD OF THE INVENTION

The present invention relates to implantable medical devices and methods, and more particularly, to an implantable cardioverter-defibrillator (ICD) having an early charging capability. Such capability reduces the time it takes to receive a higher energy shock of a tiered shock therapy when a heart has not responded to a lower energy shock.

BACKGROUND OF THE INVENTION

It is known in the ICD art to provide a "tiered" therapy with regard to the termination of sensed tachyarrhythmias. The term "tiered" therapy has been used typically to describe the different tachyarrhythmia rate zones, such as low rate ventricular tachycardia (VT Low), high rate tachycardia (VT High), and ventricular fibrillation (VF). The term "tiered therapy" also has been used to describe the increasing degree of aggressiveness within each rate zone. For example, within each zone the physician may program the number of stimulation pulses, the interval between stimulation pulses, the energy level of the stimulation, and the number of attempts, etc. Thus, based upon the detected rate of the arrhythmia, the ICD will continue to increase the level of aggressiveness until such arrhythmia is terminated.

For example, upon sensing a low rate ventricular tachycardia, an ICD may attempt to terminate such tachycardia by first applying a prescribed type of antitachycardia ("antitach") pacing. Such antitach pacing typically includes burst pacing, ramp pacing, and/or scanning pacing, as is known in the art. See, e.g., U.S. Pat. Nos. 4,427,011 and 4,541,430 (burst pacing); 4,398,536 (ramp pacing); and 5,103,822 (scanning pacing); which patents are incorporated herein by reference. If the antitach pacing is unsuccessful, the ICD may be programmed to apply a low energy, cardioversion energy shock in an attempt to cardiovert the heart. If the low energy cardioversion shock is unsuccessful, the ICD may apply a higher energy shock in an attempt to cardiovert the heart. If the tachycardia accelerates to ventricular fibrillation, the system will then apply a high energy defibrillation shock with starting values typically on the order of 10 joules and increasing up to 40 joules.

It should be noted that the basic difference between cardioversion and defibrillation is the type of arrhythmia being detected. That is, the term "cardiovert" or "cardioversion" refers to the application of energy shock treatment to a heart in response to a sensed ventricular tachycardia in an attempt to terminate the tachycardia. The term "defibrillate" or "defibrillation," on the other hand, refers to the application of energy shock treatment to a heart in response to a sensed ventricular fibrillation in an attempt to terminate the fibrillation. Cardioversion is often thought of as being "low energy" since the heart has been known to successfully convert the arrhythmia with electrical shocks in the range of 0.1 to 10 joules. However, it is still classified as cardioversion if the arrhythmia is a ventricular tachycardia even if the energy required to convert the arrhythmia goes up to the maximum value (e.g., 40 joules). Defibrillation, on the other hand, is often thought of as being "high energy" since the heart has been successfully defibrillated with energy shocks in the range of 10 to 40 joules. In contrast, the pacing pulses that are applied to a heart during normal or antitach pacing are typically of much lower energy (e.g., between 50 and 200 micro joules). The principal difference between the types of therapy provided by an ICD supporting tiered therapy is that of arrhythmia detection and the programmed level of aggressiveness with the therapy typically starting by applying the lowest energy stimulation for that detected arrhythmia and working its way up to high energy shock therapy, as required.

The energy shock, whether cardioversion or defibrillation, is delivered to the heart via what is commonly referred to as "defib leads," "defibrillation lead or electrode," or "patch electrodes." However, it is recognized that the electrode system could also be epicardial electrodes (attached to the external surface of the heart) or endocardial (attached to the internal surface of the heart) or any combination of patch, epicardial or endocardial. Such electrodes are well known in the art. See, for example, U.S. Pat. No. 4,662,377 (Heilman et al.), issued May 5, 1987, entitled "Cardioverting Method and Apparatus Utilizing Catheters and Patch Electrodes"; U.S. Pat. No. 4,481,953 (Gold et al.), issued Nov. 13, 1984, entitled "Endocardial Lead Having Helically Wound Ribbon Electrode"; and U.S. Pat. No. 4,010,758 (Rockland et al.), issued Mar. 8, 1977, entitled "Bipolar Body Tissue Electrode," which patents are hereby incorporated herein by reference. Hereinafter, the electrodes (whether patch, epicardial, or endocardial, etc.) will be referred to as simply "shocking electrodes."

In order to apply an electrical pulse to the heart (whether of low, moderate or high energy), it is first necessary to charge one or more output capacitors of the ICD device with an electrical charge of the desired energy. Typically, one set of low voltage output capacitors (which may be a single capacitor) is charged to provide the requisite energy for normal or antitach pacing. The normal pacing lead(s) is then A.C. coupled to such set of low voltage capacitors through an appropriate output switch. Another set of capacitors, which is generally a set of high voltage capacitors, is charged to provide the requisite energy for cardioversion or defibrillation. Appropriate shocking electrodes are then coupled to such set of high voltage capacitors through an appropriate high voltage output switch. When an electrical stimulation pulse is to be applied to the heart, the appropriate output switch is closed to connect the low or high voltage output capacitor(s) to the cardiac tissue through either the pacing or shocking electrodes, thereby effectively "dumping" the charge stored in the low or high voltage output capacitor(s) across the cardiac tissue.

All tiered therapy ICD's known to applicants begin to charge their output capacitor(s) following verification of the failure of the previous less aggressive therapy. For example, as soon as the ICD sensing and logic circuits determine that the first tier of therapy (e.g., antitach therapy) has not successfully terminated the tachyarrhythmia, the high voltage output capacitors are charged to the appropriate energy for a second tier of therapy (e.g., cardioversion in the case of ventricular tachycardia; or defibrillation in the case of ventricular fibrillation). As soon as the ICD sensing and logic circuits determine that the second tier of therapy has not successfully terminated the tachyarrhythmia, the high voltage output capacitors are charged to a higher energy level. Unfortunately, it may take 3-4 seconds to charge the high voltage output capacitors to a moderate energy level to (1 to 10 joules), and 7-15 seconds to charge such capacitors to a high energy level (11 to 40). Disadvantageously, these charging times represent a significant period of time, or "time-to-therapy," during which the tachyarrhythmia continues without the benefit of having the ICD apply any therapy. Furthermore, as the duration of the tachyarrhythmia lengthens, it becomes increasingly more difficult to terminate the arrhythmia with an electrical stimulus. Thus, what is needed is an ICD device wherein the time-to-therapy is reduced, thereby reducing the exposure of the patient to the tachyarrhythmia, and thereby increasing the probability of success of the cardioversion-defibrillation attempt.

SUMMARY OF THE INVENTION

The present invention addresses the above and other needs by providing an implantable cardioverter-defibrillator (ICD) that automatically uses the least aggressive therapy of a tiered therapy as it attempts to terminate tachyarrhythmias, and in so doing, employs an early charging feature to reduce the "time-to-therapy." The ICD of the invention includes sensing and logic circuits to sense a tachyarrhythmia through one or more sensing and/or shocking electrodes. The ICD also includes low and high voltage output capacitors that store an appropriate energy suitable for a selected therapy. A charging circuit charges the output capacitors to the appropriate energy, and an output switch selectively connects the output capacitors to the appropriate pacing or shocking electrodes. The operation of the ICD is controlled by a control circuit. The control circuit controls, among other things, when the low or high voltage output capacitors are charged, the energy level to which such capacitors are charged, and when the output switch connects such capacitors to cardiac tissue through the pacing or shocking electrodes.

Like ICD's of the prior art, the present invention begins with a less aggressive (lower energy) therapy according to the sensed tachyarrhythmia and increases aggressiveness accordingly. For example, in the presence of a tachycardia, the ICD of the present invention may first apply antitachycardia pacing (a prescribed burst or sequence of low energy pacing pulses), if so programmed, in an attempt to terminate the sensed tachycardia. If the tachycardia persists, the ICD may advance to a cardioversion (initially, a low energy shock with increasing energy shocks until terminated). Whenever the ICD detects ventricular fibrillation, the ICD will apply a defibrillation pulse (a high energy shock).

Unlike ICD's of the prior art, however, the control circuit of the ICD of the present invention causes the high voltage output capacitors of the ICD (used to store the energy that is applied during cardioversion or defibrillation) to begin charging during the application of the less aggressive therapy, or during the interval immediately following a prior therapy attempt during which the ICD sensing and logic circuits attempt to verify the successful termination of the tachyarrhythmia. In this manner, the needed cardioversion or defibrillation therapy may be applied immediately following confirmation of the failure of a less aggressive (lower energy) therapy, without having to wait while the high voltage output capacitors are charged. Hence, the time-to-therapy is significantly reduced, advantageously increasing the probability of success of the cardioversion-defibrillation attempt and reducing the exposure of the patient to the tachyarrhythmia.

An ICD made in accordance with the present invention may thus be characterized as including a sensing circuit that senses electrogram (EGM) signals through a sensing lead coupled to a patient's heart; control logic and timing circuits that determine whether the EGM signals sensed by the sensing circuit are indicative of a tachyarrhythmia; and a pulse generator that selectively generates stimulation pulses of a first energy in a prescribed pattern as controlled by the control logic and timing circuits. The stimulation pulse of the first energy is applied to the patient's heart through the sensing lead in an attempt to terminate the sensed tachyarrhythmia. The ICD also includes at least one shocking electrode coupled to the patient's heart; and a cardioversion-defibrillation circuit that selectively generates stimulation pulses of a second energy as controlled by the control logic and timing circuits. The stimulation pulses of the second energy are applied to the patient's heart through the shocking electrode(s) in a further attempt to terminate the sensed tachyarrhythmia. That is, the control logic and timing circuits are configured to terminate the sensed tachyarrhythmia in accordance with a tiered therapy (i.e., with increasing aggressiveness according to the detected arrhythmia).

The tiered therapy includes a first tier (e.g., antitach pacing) that applies the stimulation pulses of the first energy (e.g., a level safely above stimulation threshold) in response to sensing a given tachycardia, and a second tier (e.g., cardioversion) that applies the stimulation pulses of the second energy (e.g., low or moderate amplitude cardioversion shocks) immediately after determining that the first tier could not successfully terminate the tachycardia. In this manner, in the event the first tiered therapy does not terminate the tachycardia, the second tier of therapy is immediately applied.

In accordance with one aspect of the above-characterized invention, the cardioversion-defibrillation circuit further selectively generates stimulation pulses of a third energy (e.g., higher amplitude shocks) as controlled by the control logic and timing circuits. The stimulation pulses of the third energy are also applied to the patient's heart through the shocking electrode(s). Thus, the tiered therapy further includes a third tier (e.g., high energy shock cardioversion or defibrillation) that applies the stimulation pulses of the third energy as soon as possible after determining that the sensed tachyarrhythmia was not terminated by the second tier.

The invention, in accordance with another aspect thereof, may be characterized as an ICD having (a) sensing and logic circuits to sense a tachyarrhythmia through one or more sensing and shocking electrodes coupled to a patient's heart; (b) low and high voltage output capacitors coupled to the sensing and shocking electrodes, respectively, through an output switch; (c) a charging circuit that charges the output capacitors to a specified energy; and (d) a control circuit that generates control signals. In operation, the control signals are coupled to the charging circuit and output switch for the purpose of controlling the charging of the low and high voltage output capacitors, as well as the closure of the output switch, in accordance with a prescribed tiered therapy. The tiered therapy includes a therapy phase during which a less aggressive therapy is applied through at least one of the sensing or shocking electrodes, followed by a verification phase during which a determination is made if the less aggressive therapy was successful in terminating a sensed tachyarrhythmia. If not successful, the verification phase is followed immediately by a more aggressive therapy applied through at least one of the sensing or shocking electrodes. Advantageously, the control circuit of the ICD further includes reduced time-to-therapy means for charging the high voltage output capacitors to a prescribed energy at the same time as a specified one of the therapy phase or the verification phase is being carried out in accordance with the prescribed tiered therapy. Thus, the ICD automatically uses the least aggressive therapy of the prescribed tiered therapy as it attempts to terminate tachyarrhythmias, and in doing so, advantageously employs an early charging feature to reduce the time-to-therapy.

The present invention may further be characterized as a method of operating an ICD, where the ICD has output means for delivering an electrical shock of a prescribed energy to the heart of a patient and means for sensing a tachyarrhythmia of the patient's heart. Such method comprises the steps of: (a) sensing a tachyarrhythmia; (b) issuing a first therapy comprising an electrical shock of a first energy in an attempt to terminate the sensed tachyarrhythmia; (c) checking to see if the first therapy was successful in terminating the tachyarrhythmia; (d) charging a high voltage output capacitor of the ICD to a specified charge level in anticipation of applying a second therapy comprising an electrical shock of a second energy, the second energy being greater than the first energy, the charging of the high voltage output capacitor for application of the second therapy being commenced simultaneously with the checking of step (c); and (e) issuing the second therapy as soon as the charging of step (d) has been completed, and as soon as a determination has been made in step (c) that the first therapy was not successful.

The method summarized above may be extended, as required, to include the additional steps of: (f) checking to see if the second therapy was successful in terminating the tachyarrhythmia; (g) charging the high voltage output capacitor of the ICD to a different specified charge level in anticipation of applying a third therapy comprising an electrical shock of a third energy; and (h) issuing the third therapy as soon as the charging of step (g) has been completed, and as soon as a determination has been made in step (f) that the second therapy was not successful. In carrying out this method, the third energy is greater than the second energy, and the charging of the high voltage output capacitor for application of the third therapy is commenced simultaneously with the checking of step (f).

It is thus a feature of the invention to provide a tiered-therapy ICD that affords a reduced time-to-therapy, thereby reducing the exposure of the patient to a tachyarrhythmia, and thereby increasing the probability of a successful cardioversion-defibrillation attempt.

It is a further feature of the invention to begin charging the high voltage output capacitors of a tiered-therapy ICD during the application of a less aggressive therapy, or while the ICD is attempting to verify if a prior therapy attempt was successful, thereby allowing such capacitors to be fully charged and ready in the event a more aggressive therapy is needed.

It is another feature of the invention to provide a charging circuit for charging one or more high voltage output capacitors within a tiered-therapy ICD device that minimizes the time period required to obtain a prescribed charge on the high voltage output capacitors.

BRIEF DESCRIPTION OF THE DRAWINGS

The above and other aspects, features and advantages of the present invention will be more apparent from the following descriptions of the drawings:

FIGS. 4-1 and 4-2 show a flow diagram that illustrates the operation of the ICD of FIG. 1 in order to provide a reduced time-to-therapy in accordance with the present invention;

FIG. shows a simplified electrical schematic diagram of the rapid high voltage charging circuit used by the ICD of FIG. 1; and FIG. 6 depicts a timing waveform diagram that illustrates the basic operation of the rapid charging circuit of FIG. 5.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Typically, a tachyarrhythmia is a rapid irregular rhythm of the heart, e.g., ventricular tachycardia or ventricular fibrillation. However, for purposes of the present invention a tachyarrhythmia may also include atrial tachycardia, atrial fibrillation, as well as asystole (a stopped heart). As used hereinafter, the term "tachyarrhythmia" is used broadly to indicate any irregular rhythm of the heart that interferes with the heart's ability to perform its basic function of a pump and requires intervention by an ICD.

Figure 1:
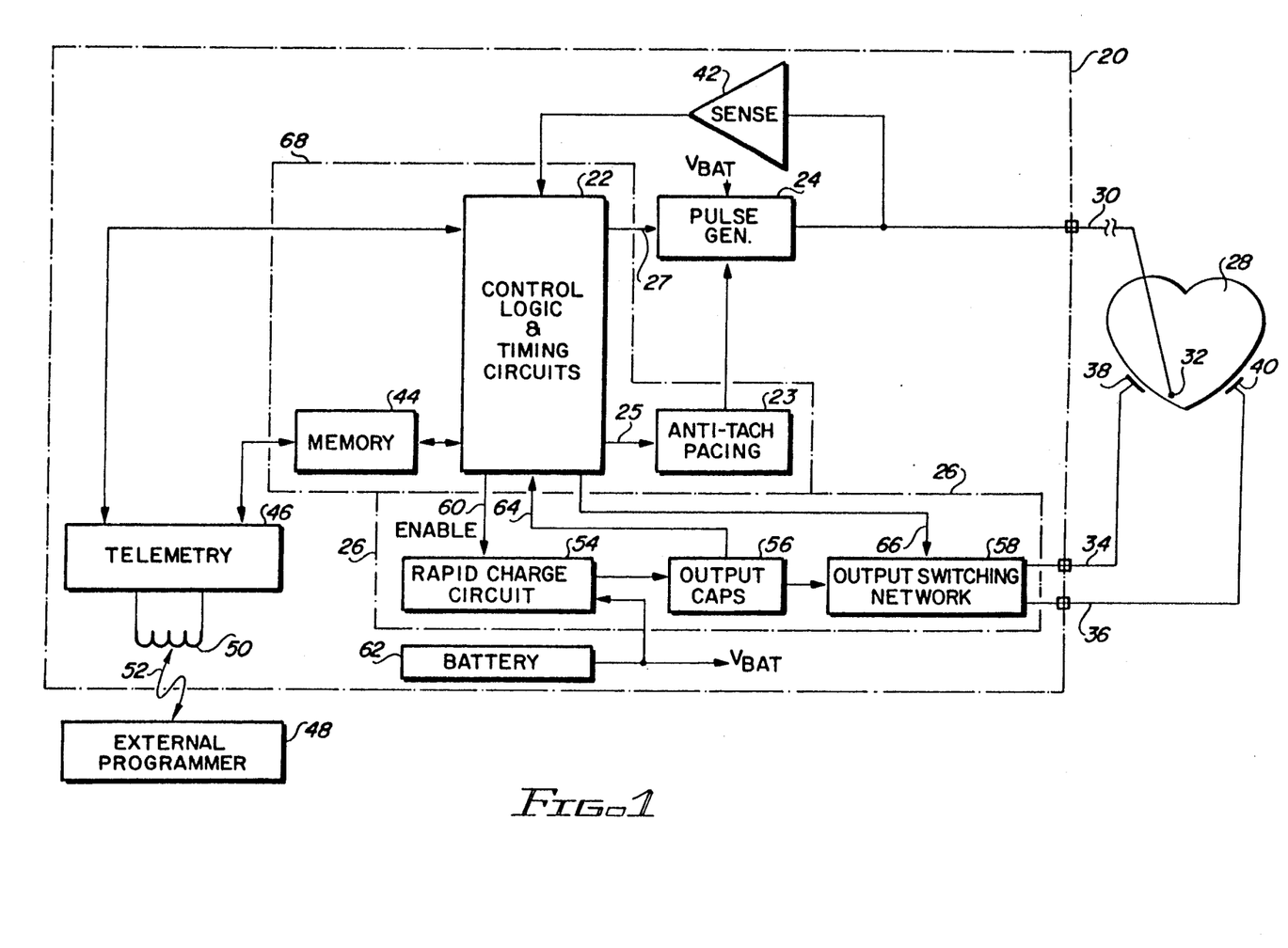
FIG. 1 shows a simplified functional block diagram of an implantable cardioverter-defibrillator (ICD) capable of providing a tiered therapy output.

It is the primary function of an implantable cardioverter-defibrillator (ICD) device to sense the occurrence of a tachyarrhythmia, and to automatically apply an appropriate therapy to the heart aimed at terminating the tachyarrhythmia. To this end, an ICD device 20 made in accordance with the present invention includes, as shown in the functional block diagram of FIG. 1, control logic and timing circuits ("control/timing" circuits) 22 that control a pulse generator 24 and a high voltage generator 26. The pulse generator 24 generates output stimulation pulses of low energy (antitach pulses), e.g., electrical pulses having an energy of less than 200 micro joules, as controlled by the control/timing circuit 22 and an antitach pacing circuit 23. Such antitach pulses are applied to a patient's heart 28 through a conventional pacing lead 30 having an electrode 32 in contact with the cardiac tissue (usually inside the right ventricle and/or right atrium). While only a single pulse generator 24 and pacing lead 30 are shown in FIG. 1, it is to be understood that the invention is not so limited and may, for example, include a second pulse generator and pacing lead, as is known in the art, to deliver dual-chamber pacing or antitach pulses to a patient's heart.

The high voltage generator 26 generates output electrical stimulation pulses of moderate (e.g., 1 to 10 joules) or high energy (e.g., 11 to 40 joules), as controlled by the control/timing circuit 22. Such energy pulses are applied to the patient's heart through at least two shocking electrodes 34 and 36, each of which is respectively coupled to a suitable shocking electrode 38 and 40. Typically, the shocking electrodes 38 and 40 are patch electrodes that are placed in contact with, or near, external cardiac tissue. The shocking electrodes 38 and 40 may be of conventional design and may be implanted using known techniques, as shown, e.g., in U.S. Pat. Nos. 4,774,952 (Smits); 4,991,603 (Cohen et al.) and 4,998,975 (Cohen et al.), incorporated herein by reference. While only two shocking electrodes and electrodes are shown in FIG. 1, it is to be understood that additional shocking electrodes may be used as desired or needed in order to efficiently and effectively apply the shock treatment generated by the high voltage generator 26 to the patient's heart 28.

The ICD 20 also includes a sense amplifier 42 that is coupled to the pacing lead 30 and electrode 32. It is the function of the sense amplifier 42 to sense the activity of the heart 28 as manifest by the presence of certain electrical signals picked up by the electrode 32. That is, as is known in the art, R-waves occur upon the depolarization, and hence contraction, of ventricular tissue; and P-waves occur upon the depolarization, and hence contraction, of atrial tissue. Thus by sensing R-waves through the sense amplifier 42 and providing such sensed signals to the control/timing circuit 22, the control/timing circuit 22 is able to make a determination as to the rate and regularity of the patient's heartbeat. Such information, in turn, allows the control/timing circuit 22 to determine whether the heart 28 is experiencing a tachyarrhythmia. (Similarly, in a dual-chamber pacing device, P-waves could be sensed by a sense amplifier (not shown) to enable the control/timing circuit 22 to make a determination as to any atrial arrhythmia.)

The control/timing circuit 22 further has a memory circuit 44 coupled thereto wherein the operating parameters used by the control/timing circuit 22 are stored. Such operating parameters may define, for example, the amplitude of the antitach and high voltage stimulation pulses that are to be generated, the type of pattern (e.g., burst, scan and/or ramp) of antitach pulses that are to be used, the timing intervals used to determine whether a tachyarrhythmia is present, and the like. Advantageously, such operating parameters may be noninvasively programmed into the memory 44 through a telemetry circuit 46 that is in telecommunicative contact with an external programmer 48 by way of a suitable coupling coil 50. The coupling coil 50 may serve as an antenna for establishing a radio frequency (RF) communication link 52 with the external programmer 48; or the coil 50 may serve as a means for inductively coupling data to and from the telemetry circuit 46 from and to the external programmer 48. Further, such telemetry circuit 46 advantageously allows status information relating to the operation the ICD 20, as contained in the control/timing circuit 22 or memory 44, to be sent to the external programmer 48 through the established link 52.

The design, operation and use of the telemetry circuit 46 and external programmer 48 to selectively program operating parameters into the memory 44, or to selectively monitor the operating status of the ICD 20, may be the same as are known in the pacing art. See, e.g., U.S. Pat. Nos. 4,809,697 (Causey, III et al.) and 4,944,299 (Silvian), incorporated herein by reference.

The control/timing circuit 22 includes appropriate logic circuits for analyzing the output of the sense amplifier 42 and determining if such signals indicate the presence of a tachyarrhythmia. Typically, such determination is made by determining the rate of the sensed R-waves and/or P-waves and comparing the determined rate against: (1) a low tachycardia reference rate; (2) a high tachycardia reference rate; (3) a maximum (fibrillation) reference rate; or (4) a minimum threshold reference rate (to determine if asystole, or a stopped heart, is present). If a tachyarrhythmia is sensed, then appropriate circuits included in the control/timing circuit 22 are triggered to apply a prescribed tiered therapy.

Figures 6, 42:
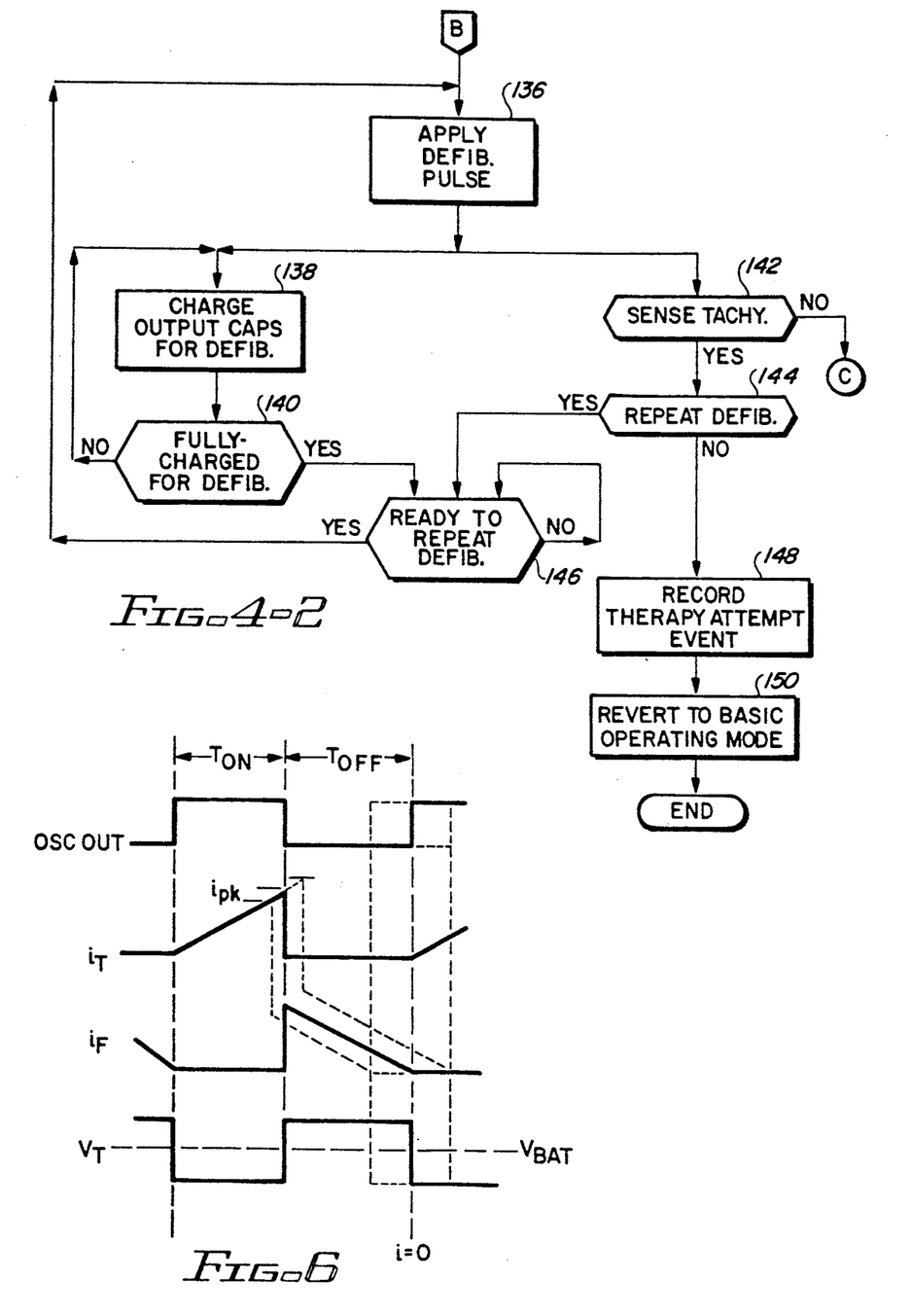
Figure 41:
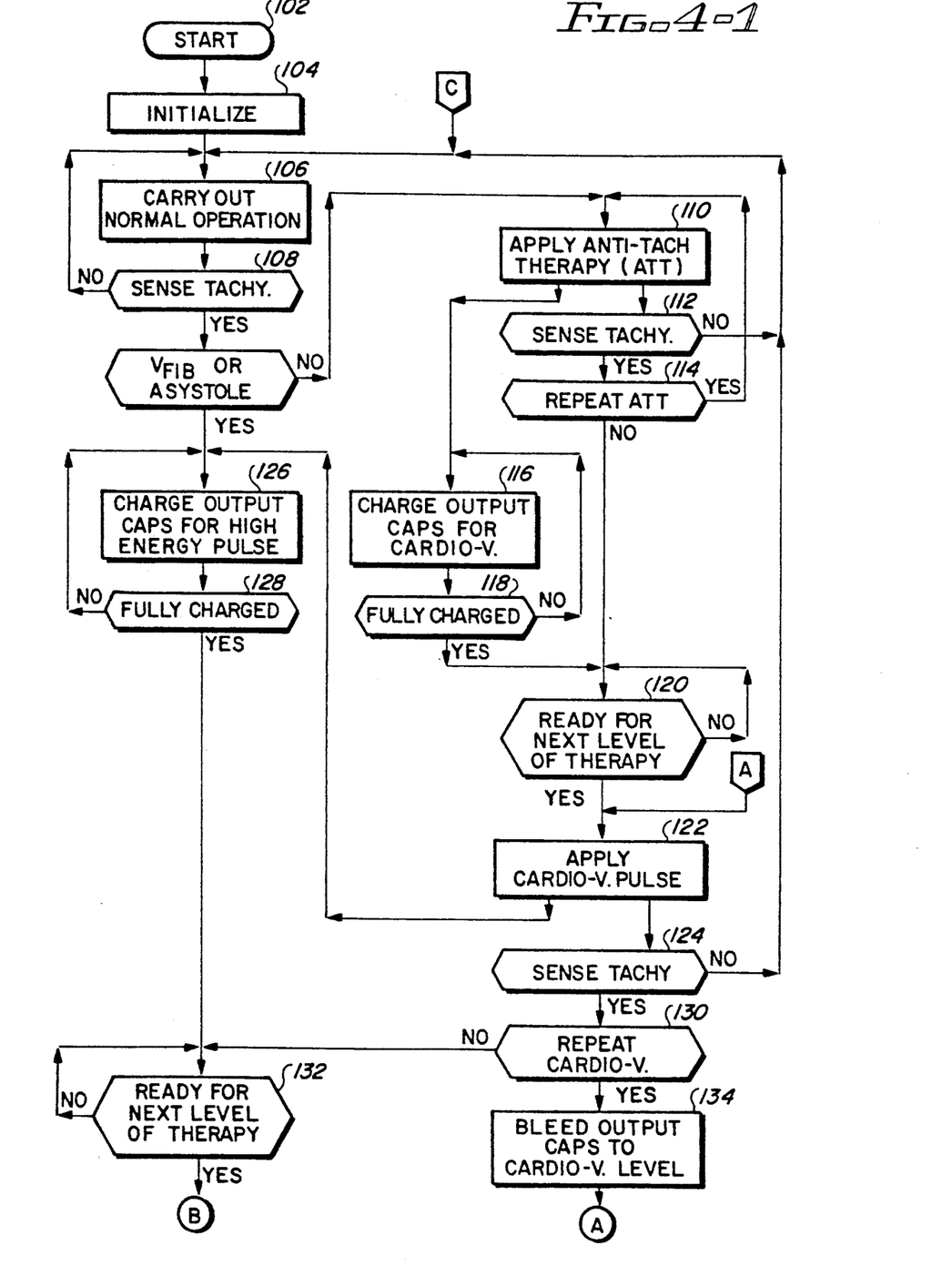

The prescribed tiered therapy may advantageously be programmed into the memory 44. A preferred tiered therapy is described below in conjunction with FIGS. 4-1 and 4-2. Basically, such tiered therapy is implemented by generating, in a controlled time sequence, a series of control signals that activate various elements or features of the invention. For example, a first control signal, appearing on signal line 25, enables the antitach pacing circuit 23. A second control signal, appearing on signal line 27, triggers the pulse generator 24 to deliver the antitach pacing defined by the antitach pacing circuit 23 at a controlled time within the cardiac cycle. (The "cardiac cycle" is the time for one complete heartbeat, and includes the depolarization of the atrium and the depolarization of the ventricle.) The antitach pacing circuit 23 defines a selected type of antitach pacing (e.g., burst pacing, ramp pacing, or scan pacing) that is delivered to the heart at the time controlled by the antitach pacing control signal 27.

Similar control signals generated by the control/timing circuit 22 control the operation of the high voltage generator 26. As seen in FIG. the high voltage generator 26 includes a rapid charge circuit 54, one or more output capacitors 56, and an output switching network 58. When the control/timing circuits 22 determine the need for a moderate or high energy output pulse, an enable signal 60 enables the rapid charge circuit 54 so that it begins to charge the output capacitor 56 using power derived from a battery 62. As the output capacitor 56 is thus charged, it is monitored via signal line 64 to determine if the charge (voltage) stored thereon is at a prescribed level. The prescribed level is defined by an appropriate charge level signal that may be programmably stored in the memory 44. Once the prescribed charge level has been reached, which may take several seconds depending upon the charge level desired, the output capacitor 56 thereafter stands ready to discharge the energy stored thereon through the output switching network 58 to the heart 28. Thus, another control signal 66 controls the output switching network 66 so as to cause the high energy stimulus stored on the output capacitor 56 to be delivered at a prescribed time.

The control/timing circuits 22, as well as the antitach circuit 23, may be implemented using conventional logic circuitry, i.e., registers and logic gates, preferably configured in a suitable state machine. The use of state machine logic circuitry to control an implantable medical device is described, e.g., as shown in U.S. Pat. No. 4,712,555 (Thornander et al.), incorporated herein by reference.

Alternatively, the control/timing circuit 22, antitach pacing circuit 23, and memory circuitry 44 may be implemented using a suitable microprocessor 68. In such instance, an operating program is stored in the memory 44 to control the operation of the processor. Typically, such operating program is permanently stored in read only memory (ROM) included as part of the memory 44 of the microprocessor 68, while certain operating parameters or variables associated with the operating program may be downloaded from the external programmer 48 to random access memory (RAM), also included as part of the memory 44. The use of a microprocessor to control an implanted medical device is described, e.g., in U.S. Pat. No. 4,940,052 (Mann et al.), incorporated herein by reference.

The pulse generator 24 of FIG. 1 may be of conventional design, such as is disclosed in U.S. Pat. No. 4,739,437 (Morgan), incorporated herein by reference. Basically, the pulse generator 22 includes an output pulse capacitor (not shown) on which a specified charge (voltage) is stored. Typically, because the charge (voltage) stored on such output pulse capacitor must be greater than the voltage available from the battery 62 included with the implantable device, a charging circuit is employed as part of the pulse generator 24 to "pump" up the voltage from the existing battery 54 to a specified voltage that is stored on the output pulse capacitor. When the stimulation pulse is to be generated by the pulse generator, an output switch is closed. The output switch connects the output pulse capacitor to the implantable lead, thereby "dumping" the charge held on the capacitor through the lead 30 and electrode 32 to desired cardiac tissue.

Those having experience in the cardioversion and defibrillation art will readily recognize that the ICD 20 shown in FIG. 1 is structurally very similar to prior art ICD's. That is, ICD's of the prior art include both a pulse generator and a high voltage output circuit for delivering a tiered therapy to cardiac tissue as controlled by an appropriate control/timing circuit. The principal difference between the ICD 20 of the present invention and prior art ICD's lies primarily in how the ICD operates, e.g., as controlled by the control/timing circuit 22, and in how the rapid charge circuit 54 is configured to charge the output capacitor 56 in a more rapid manner than has previously been achieved.

Figure 2:
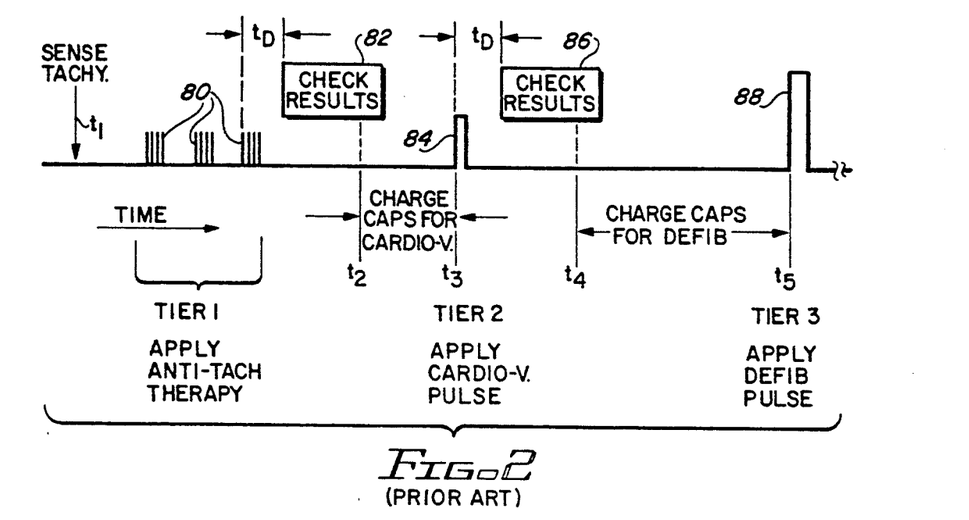
FIG. 2 is a timing diagram that diagrammatically illustrates the type of tiered output provided by the ICD of FIG. 1 when operated in accordance with the teachings of the prior art.
Figure 3:
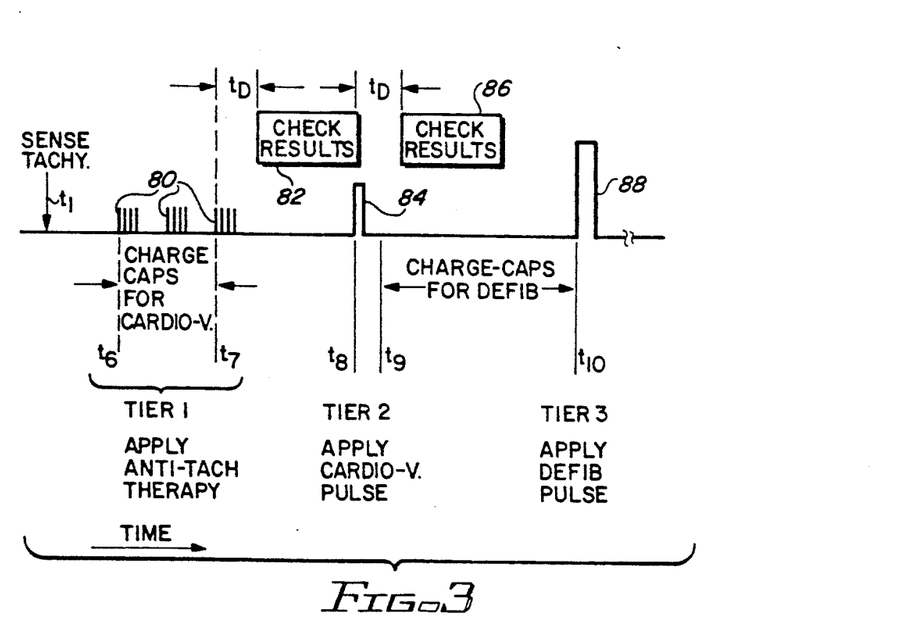
FIG. 3 is a timing diagram as in FIG. 2 that diagrammatically illustrates the tiered output of an ICD when operated in accordance with the teachings of the present invention, and illustrates how the time-to-therapy is reduced.

To better understand the operation of the ICD 20 shown in FIG. 1, and the differences between such operation and the operation of a prior art ICD, reference is next made to FIGS. 2 and 3. FIG. 2 is a timing diagram that diagrammatically illustrates the type of tiered output provided by a prior art ICD in response to a sensed tachycardia, which prior art approach may be characterized as a serial approach. As seen in FIG. 2, at time t1, a tachycardia is sensed. The ICD responds by applying a first tiered therapy, (e.g., antitach pacing) comprising three bursts 80 of stimulation pulses. A fixed time tD after the last burst 80 of pulses (which fixed time tD represents the tissue refractory time periods that follow application of any stimulation pulse), the results of the antitach pacing are checked to determine if the first tiered therapy successfully terminated the sensed tachycardia. Such checking, or verification, is performed by the sensing circuits 42 in combination with the control/timing circuits 22 (or, if used, the microprocessor 68), and is represented in FIG. 2 by the box 82, labeled CHECK RESULTS.

The verification, or checking, performed after the conclusion of the antitach pacing takes a finite time period, represented in FIG. 2 by the length of the box 82. If, as a result of such checking 82, a determination is made that the antitach pacing was not successful in terminating the tachycardia, then, in anticipation of applying a second tiered therapy, the output capacitor is charged to a level suitable for delivery of a moderate energy level (e.g., 0.1 to 10 joules) cardioversion pulse. Such charging begins at time t2 and is not completed until time t3. As soon as the output capacitor is charged to the specified level for a cardioversion pulse, i.e., at time t3, a cardioversion pulse 84 is delivered (i.e., the output capacitor is discharged across the cardiac tissue, resulting in the cardioversion pulse 84).

Following delivery of the cardioversion pulse 84 and an associated delay tD, the results of the application of the cardioversion pulse 84 are checked, represented by the CHECK RESULTS box 86. If, as a result of such checking 86, a determination is made that the cardioversion pulse was not successful in terminating the tachycardia or if the tachycardia accelerated into ventricular fibrillation, then, in anticipation of applying a third tiered therapy, the output capacitor is charged to a higher energy level pulse. Such charging begins at time t4 and is not completed until time t5. As soon as the output capacitor is charged to the specified level, i.e., at time t5, a higher energy level pulse 88 is delivered (i.e., the output capacitor is discharged across the cardiac tissue, resulting in the higher energy level pulse 88).

Thus, it is seen in FIG. 2 that the prior art serial approach is to apply a first tiered therapy (e.g., antitach pacing with burst pacing) and check to see if it was successful. If not, the output capacitor is charged in anticipation of applying a second tiered therapy (e.g., cardioversion pulse). As soon as the output capacitor is charged, the second tiered therapy (e.g., a low or moderate energy level cardioversion pulse) is applied, and the results are checked to see if successful. If not, the output capacitor is again charged in anticipation of applying a third tiered therapy (e.g., a high energy pulse). As soon as the output capacitor is charged sufficiently to deliver the high energy level pulse, the third tiered therapy is finally applied. Unfortunately, due to the relatively long time that it takes to charge the output capacitor sufficient for delivery of a cardioversion or defibrillation pulse, the time-to-therapy is correspondingly long. Because of this long time-to-therapy, the therapy that is eventually applied may not be as successful as it might have been if it could have been applied sooner.

In contrast to the serial approach of applying a tiered therapy shown in FIG. 2, the present invention utilizes a parallel tiered therapy approach as shown in FIG. 3. Advantageously, using the approach shown in FIG. 3, the time-to-therapy is significantly reduced, even through the individual events that must occur (e.g., certain refractory delays tD, and capacitor charge times) are generally the same.

Referring to FIG. 3, it is seen that a tachycardia is sensed at time t1, and the first tiered therapy (e.g., antitach pacing, as represented by the application of three bursts 80 of stimulation pulses) is applied in response thereto, just as in the prior art approach shown in FIG. 2. Unlike the prior art approach, however, the present invention begins to charge the output capacitor 56 in anticipation of delivering the second tiered therapy (e.g., a low or moderate energy level cardioversion pulse) at time t6, which is in parallel with the commencement of the first tiered therapy. Thus, while the first tiered therapy is being applied, the output capacitor(s) is being charged in anticipation of applying the second tiered therapy. Hence, at the completion of the first tiered therapy, and after the requisite refractory delay tD, and as soon as a verification can be made that the first tiered therapy was not successful in terminating the tachyarrhythmia (i.e., at the conclusion of the CHECK RESULTS event 82 at time t8), the second tiered therapy (application of the cardioversion pulse 84) can be immediately applied.

Still referring to FIG. 3, it is seen that soon after the cardioversion pulse 84 has been applied (i.e., beginning at time t9), the output capacitor is again charged in anticipation of applying the third tiered therapy (e.g., a high energy level cardioversion or defibrillation pulse). Thus, while the output capacitor is being charged, the results of the second tiered therapy may be checked, as represented by the CHECK RESULTS event 86, at the conclusion of the delay tD. Hence, the verification of the second tiered therapy proceeds simultaneously with the charging of the output capacitor. As a result, as soon as the output capacitor is charged, at time t10, the third tiered therapy—application of the high energy pulse 88—may immediately occur.

Note that as illustrated in FIG. 3, the charging of the output capacitor in anticipation of delivering the second tiered therapy (i.e., the low to moderate energy level cardioversion pulse) is completed at a time t7 which is prior to the completion of the application of the first tiered therapy and its verification. Hence, it is the completion of the verification of the first tiered therapy (the end of CHECK RESULTS 82) that limits the time when the second tiered therapy may be applied. However, in some applications, it may be desirable to begin the charging of the output capacitor during the verification of the first tiered therapy, (i.e., at the beginning of the CHECK RESULTS 82) in order to reduce the drain on the battery, or for other reasons. In such event, the charging of the output capacitor may not be completed prior to the completion of the verification of the first tiered therapy, and the second tiered therapy will thus not be able to be applied until the output capacitor has been charged. In other words, whichever of the two parallel events or sequences (the charging of the output capacitor or the verification of the prior tiered therapy) concludes last determines when the next tiered therapy may be applied.

The above discussion also applies to the charging of the output capacitor in anticipation of delivering the third tiered therapy. That is, it is the longest of two parallel events or sequences—the charging of the output capacitor or the verification of the second tiered therapy—that limits when the third tiered therapy may be applied. As suggested by the timing diagram of FIG. 3, the charging of the output capacitor in anticipation of delivering the high energy pulse 88 may be significantly longer than verifying whether the second tiered therapy was successful in terminating the tachyarrhythmia. However, such may not always be the case, particularly if the CHECK RESULTS 86 involves several checks and cross-checks.

It is further noted that the tiered therapy that is applied in accordance with the present invention need not necessarily be a "single shot" therapy as suggested in FIGS. 2 and 3. That is, FIG. 3 shows that three bursts of pulses 80 are applied (first tiered therapy) and are found to be unsuccessful; so a single cardioversion pulse 84 is applied (second tiered therapy), is found to be unsuccessful; so a single high energy level pulse 88 is applied (third tiered therapy). That is, as shown in FIG. 3, each tiered therapy is applied only once. However, it is to be understood that the present invention contemplates that each tiered therapy may be applied a programmed number of times, e.g., from one to ten, before advancing to the next (more aggressive) tiered therapy.

While the embodiment illustrated in FIGS. 2 and 3 is an example of one type of response by the ICD to a tachycardia, it is but one of many possible programmable therapies available. For example, the first, second and third tiered therapies might comprise a low, moderate and high amplitude cardioversion pulse in response to the atrial or ventricular tachycardia. As another example, the first, second and third tiered therapies might comprise a low, moderate and high amplitude defibrillation pulse in response to ventricular fibrillation or asystole. It is apparent to one skilled in the art that there are numerous programmable combinations of antitach pacing, cardioversion and defibrillation regimes possible. Whatever the desired therapy is, the present invention will begin charging the output capacitor(s) in anticipation of applying the next tiered therapy in parallel with the application of the present tiered therapy.

Thus, as seen in FIG. 3, the present invention achieves a reduced time-to-therapy by allowing certain events (such as the charging of the output capacitor) to begin and proceed while other events are still taking place (e.g., while the delivery of a lower level, less aggressive therapy is taking place), and/or while the verification of the lower level therapy is occurring.

In operation, it is thus seen that the present invention applies a "therapy phase" and a "verification phase." The therapy phase comprises charging the output capacitor in anticipation of applying the particular tiered therapy and the application of such tiered therapy. The verification phase comprises checking the sensing circuits after the therapy phase has been completed to determine if the therapy phase was successful in terminating the sensed tachyarrhythmia. The present invention recognizes and takes advantage of the fact that the therapy phase and the verification phase need not necessarily proceed in series. Rather, the therapy phase for a more aggressive therapy may begin while the therapy phase or verification phase of a less aggressive phase is still proceeding.

In addition to the reduced time-to-therapy achieved by using the parallel approach shown in FIG. 3, it is significant to note that the present invention also reduces the time-to-therapy by using a rapid charge circuit 54 that is able to place a given charge on the output capacitor 56 in a shorter time than has heretofore been achievable. Such rapid charge circuit 54 is described more fully below in conjunction with the explanation of FIGS. 5 and 6.

Referring next to FIGS. 4-1 and 4-2, there is shown a flow diagram that illustrates the operation of the ICD of FIG. 1 in order to provide a reduced time-to-therapy in accordance with the present invention. FIGS. 4-1 and 4-2 should be considered as the same figure, with portions thereof being shown on one drawing sheet, and other portions thereof being shown on another drawing sheet. Each main step of the operation shown in FIGS. 4-1 and 4-2 is represented as a block or box, having a corresponding reference numeral. Rectangular-shaped boxes or blocks represent a process or event or series of events that occur, and diamond-shaped (or hexagonal-shaped) boxes or blocks represent a determination or decision that is made that may have at least two outcomes, e.g., YES or NO. Circles and pentagonal-shaped boxes are simply connections from one location to another, with circles representing connections on the same drawing sheet, and pentagonal-shaped boxes representing connections between drawing sheets. Oval-shaped blocks or boxes signify the start or end of the reduced timed to therapy operation.

As depicted in FIG. 4-1, after the reduced time-to-therapy operation is started (block 102), the ICD is initialized (block 104). Such initialization involves retrieving all the requisite operating parameters from the memory 44, or equivalent storage device, or otherwise setting all the necessary operating parameters needed to carry out the operation. Such operating parameters define, for example, the type of the antitach pacing to be applied; the energy of the stimulation pulses to be used in antitach pacing; the number of times antitach pacing is to be applied as a first tier in the tiered therapy before stepping up to the next tier in the tiered therapy; the energy of the cardioversion pulses; the number of cardioversion pulses to be applied as a second tier in the tiered therapy before stepping up to the last tier in the tiered therapy; the energy of the defibrillation pulses to be used; and the like.

Once initialization has been completed, the normal operation of the ICD is carried out (block 106). The normal operation of the ICD, for purposes of the present invention, involves monitoring the heart activity to determine if a tachyarrhythmia is sensed (block 108). If no tachyarrhythmias are sensed, then the ICD is essentially in a "wait" state, and nothing happens until a tachyarrhythmia is sensed. [It is noted that some ICD's also include pacing capabilities, and thus provide pacing pulses on demand, as required, in order to support a basic or sensor-indicated pacing rate, just as pacemakers do. The present invention may be used with such dual-function pacers/ICD's; and if so, the normal operation, defined in block 106, includes carrying out the pacemaker operations, as are known in the art. See, e.g., U.S. Pat. No. 4,989,602 (Sholder et al.), incorporated herein by reference.]

If a tachyarrhythmia is sensed (YES branch of block 108), then a determination is made (block (109) as to whether the tachyarrhythmia is a (1) tachycardia, either fast or slow, (2) fibrillation or asystole. If it's a tachycardia, then the first tier of the tiered therapy is applied, e.g., antitach therapy (ATT) pacing (block 110).

Two events occur after applying ATT pacing (block 110). First, in anticipation of stepping up to the next level of tiered therapy, the charging of the output capacitors is initiated (block 116). Such charging continues until the output capacitor is fully charged sufficiently to deliver a cardioversion (Cardio-V) pulse (block 118). Second, a determination is made as to whether a tachyarrhythmia is still sensed (block 112). If not (NO branch of block 112), then that indicates that the ATT pacing was successful in terminating the ta-chyarrhythmia, and the operation of the ICD returns to its normal operation (block 106). If a tachyarrhythmia is still sensed (YES branch of block 112), then a determination is made as to whether ATT pacing should be repeated (block 114). Such determination is made based on the programmed number of times that the first tiered therapy is to be applied before stepping up to the second tiered therapy. If ATT pacing is to be repeated (YES branch of block 114), then the ICD again applies the ATT pacing (block 110). If ATT pacing is not to be repeated (NO branch of block 114), then the operation of the ICD is ready to step up to the next tier of the tiered therapy (block 120), providing that the output capacitor is fully charged (YES branch of block 118).

Thus, as soon as both the output capacitor is fully charged (blocks 116,118), and a determination is made that the first tiered therapy (ATT pacing) is not to be repeated (block 114), the operation of the ICD is ready to apply the second tier of the tiered therapy (block 120).

The second tier of the tiered therapy for the ICD being described in FIGS. 4-1 and 4-2 is the application of a cardioversion pulse (block 122). After application of the cardioversion pulse, two events occur. First, in anticipation of stepping up to the next level of tiered therapy, the charging of the output capacitors is initiated (block 126). Such charging continues until the output capacitor is fully charged sufficiently to deliver a defibrillation (defib) pulse (block 128). Second, a determination is made as to whether a tachyarrhythmia is still sensed (block 124). If not (NO branch of block 124), then that indicates that the cardioversion pulse was successful in terminating the tachyarrhythmia, and the operation of the ICD returns to its normal operation (block 106). If a tachyarrhythmia is still sensed (YES branch of block 124), then a determination is made as to whether another cardioversion pulse should be applied (block 130). Such determination is made based on the programmed number of times that the second tiered therapy is to be applied before stepping up to the third tiered therapy. If another cardioversion pulse is to be applied (YES branch of block 130), then the output capacitor(s), which may be charged for delivering a high energy pulse, are bled of any excess charge in order to reduce the charge to that required for a cardioversion pulse (block 134). Then, the cardioversion pulse is again applied (block 122). If another cardioversion pulse is not to be repeated (NO branch of block 130), then the operation of the ICD is ready to step up to the next tier of the tiered therapy (block 132), providing that the output capacitor is fully charged (YES branch of block 128)

Hence, as soon as both the output capacitor is fully charged and a determination is made at block 130 that the second tiered therapy (a cardioversion pulse) is not to be repeated, the operation of the ICD is ready to apply the third tier of the tiered therapy (block 132).

The third tier of the tiered therapy for the ICD being described in FIGS. 4-1 and 4-2 is the application of a high energy pulse for defibrillation/cardioversion (block 136, FIG. 4-2). After application of the high energy pulse, two events occur. First, in anticipation of delivering another high energy pulse, the charging of the output capacitors is again begun (block 138). Such charging continues until the output capacitor is fully charged sufficiently to deliver a high energy pulse (block 140). Second, a determination is made as to whether a tachyarrhythmia is still sensed (block 142). If not (NO branch of block 142), then that indicates that the high energy pulse was successful in terminating the tachyarrhythmia, and the operation of the ICD returns to its normal operation (block 106). If a tachyarrhythmia is still sensed (YES branch of block 142), then a determination is made as to whether another high energy pulse should be applied (block 144). Such determination is made based on the programmed number of times that the third tiered therapy is to be applied before the ICD ceases the application of the tiered therapy. If another high energy pulse is to be applied (YES branch of block 144), then a determination is made as to whether the output capacitor has been charged (block 146). If not, the ICD waits until the capacitor is charged (NO branch of block 146). If yes, then the high energy pulse is again applied (block 136).

If another high energy pulse is not to be repeated (NO branch of block 144), then the ICD records that a therapy attempt was made (block 148). For example, an appropriate flag is set in a prescribed location in the memory 44, which flag may also be time-stamped, so that a physician who subsequently examines the patient and the ICD, can readily determine that the tiered therapy was applied and the time that it was applied. Thereafter, the ICD reverts to a basic operating mode (block 150), which may be, e.g., to deliver only a single therapy in response to sensing a tachyarrhythmia, thereby terminating or ceasing operation of the ICD in accordance with a tiered therapy mode (block 152).

If however, the determination made (block 109) is fibrillation or asystole, then the first tier of the tiered therapy is the application of a defibrillation pulse (block 126 and 128). Then the second and third tier of tiered therapy would consist of progressively higher level energy shocks until the fibrillation or asystole is terminated.

It is noted that the flowcharts shown in FIGS. 4-1 and 4-2 specifically describe the tiered therapy which is illustrated in FIG. 3, in which the first tiered therapy is antitach pacing, the second tiered therapy is cardioversion and the third tier is high energy shock (either defibrillation or cardioversion). Hence, the flowcharts illustrate but one possible combination of tiered therapy. The present invention is not limited as to the type of therapy delivered and that other combinations of therapy are within the spirit of the invention.

Figure 5:
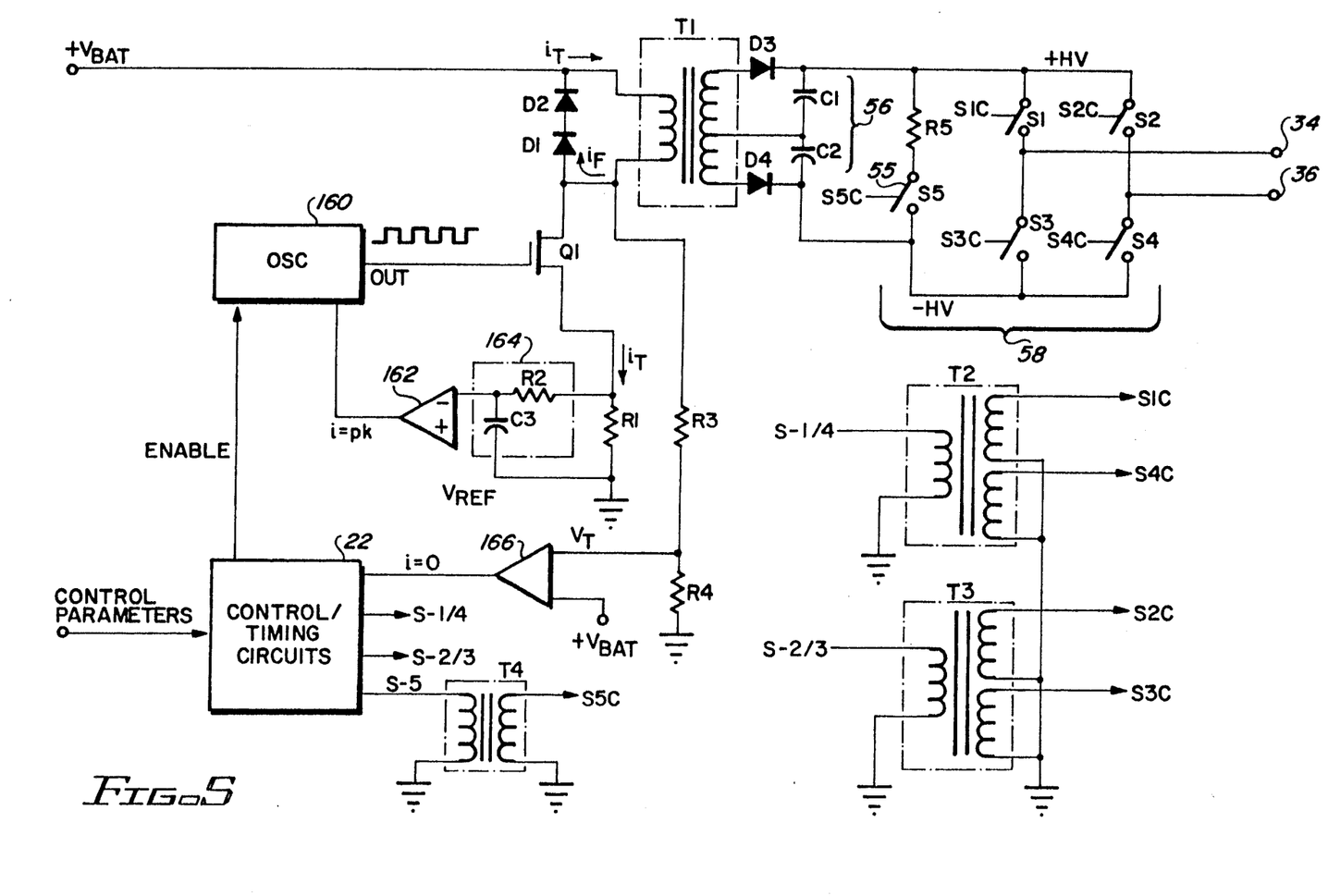

Turning next to FIG. 5, there is shown a simplified electrical schematic diagram of the rapid high voltage charging circuit 54 used by the ICD of FIG. 1. Also shown in FIG. 5 are the output capacitors 56 and the output switching network 66. The output capacitors 56, for the configuration shown in FIG. 5, comprise two capacitors C1 and C2. The capacitors are charged through a transformer T1 as described below. The capacitor C1 is connected between a midpoint of a secondary winding of the transformer T1 and a positive high voltage bus (+HV bus). The capacitor C2 is similarly connected between the same mid point of the secondary winding of the transformer T1 and a negative high voltage bus (−HV bus). A resistor R5 and a switch S5 are shunted across the output capacitor 56 to provide a means for controlling the charge level on the capacitor 56. Such discharge resistor R5 also is used as an accurate dump resistor. That is, by closing the switch S5 for a known period of time, the value of the output capacitor 56 may be accurately determined. This is important because it allows the energy stored on the output capacitor 56 to be consistent, even through the value of the capacitor 56 may change somewhat over time. Note that the switch S5 is controlled by a control signal S5C.

Still referring to FIG. 5, it is seen that the output switching network 58 comprises an array of switches S1, S2, S3 and S4 connected between the +HV bus and the −HV bus in a classical, commonly known "H" configuration. The load, i.e., the electrodes 38 and 40 placed on the patient's heart 28 (FIG. 1), is connected as the horizontal leg of such "H" configuration. Switch S1 is placed in the left upper branch of the "H" configuration; switch S2 is placed in the right upper branch; switch S3 is placed in the lower left branch; and switch S4 is placed in the lower right branch.

When a cardioversion or defib pulse is to be applied across the heart, only two switches of the "H" configuration are closed, one from the left side and one from the right side. If switches S1 and S4 are closed, for example, the high voltage pulse is applied across the load (heart) with the lead 34 and electrode 38 being positive relative to the lead 36 and electrode 40. In contrast, if switches S2 and S3 are closed, the high voltage pulse is applied across the heart with the lead 34 and electrode 38 being negative relative to the lead 36 and electrode 40. Thus, through selective control of the switches S1, S2, S3 and S4, the polarity of the high voltage pulse applied across the heart can be changed. Note that switches S1, S2, S3 and S4 are controlled by control signals S1C, S2C, S3C and S4C, respectively.

Still referring to FIG. 5, diodes D3 and D4 are used to rectify the signal appearing at the secondary winding of the transformer T1 before such signal is applied to the output capacitor 56. A primary winding of the transformer T1 is connected between the battery voltage, VBAT, on one end, and a switch, realized with transistor Q1, in series with a current sensing resistor R1 on the other end. The switch Q1 is switched ON and OFF as controlled by the output from an oscillator circuit 160. The switched end of the transformer T1 is also coupled to ground through resistors R3 and R4, connected in series. The resistors R3 and R4 function as a voltage divider that allows the voltage developed at the primary winding to be monitored. The voltage appearing between resistors R3 and R4 is referred to as the transformer voltage VT. The voltage VT is compared with the battery voltage VBAT by a comparator circuit 166. It is the function of the comparator circuit 166 to determine when the current flowing through the primary winding of the transformer is zero, as explained more fully below in conjunction with FIG. 6.

Two diodes D1 and D2 are connected in series across the primary winding of the transformer T1 so as to clamp the voltage appearing at the switched end of the transformer to no more than two forward-biased diode voltage drops (approximately 1.4 volts) above the battery voltage, VBAT, when the transistor switch Q1 is opened.

The voltage developed across the current sense resistor R1 is a function of the transformer current, iT. This voltage is monitored through a one-pole filter 164, comprising resistor R2 and capacitor C3, and compared to a programmable reference voltage VREF by a comparator circuit 162. The output of the comparator circuit 162 is directed to the oscillator 160. It is the function of the comparator circuit 162 to determine when the transformer current iT (or more precisely the voltage developed across R1 as a result of the transformer current iT) is at a peak value as defined by the reference voltage VREF. When the transformer current reaches the specified peak value, the oscillator changes its output signal state, as explained more fully below in FIG. 6, which causes the switch Q1 to turn OFF.

The operation of the rapid charging circuit is illustrated with reference to FIG. 6, which depicts a timing waveform diagram of the output of the oscillator 160, the transformer current iT, the flyback transformer current iF, and the transformer voltage VT. As evident from FIG. 5, when the output of the oscillator is high, the switch Q1 is ON, and the transformer current iT begins to flow through the primary winding of the transformer T1 Due to the large inductance of the transformer winding, the current iT linearly increases, as shown in FIG. 6. As soon as the current iT reaches a specified peak value, ipk, as sensed by the peak detector 162, the output of the oscillator is forced low, causing the switch Q1 to turn OFF.

As soon as the switch Q1 is turned OFF, the current iT sensed in the sensing resistor R1 goes to zero. However, the current flowing through the transformer winding cannot suddenly go to zero, but rather must ramp back down to zero. As it ramps back to zero it is referred to as the flyback current iF. The flyback current iF, as it ramps back to zero, starts at the same value as ipk. The diodes D1 and D2 provide a current path for the flyback current iF, and the presence of the current iF causes the voltage VT to increase above the battery voltage VBAT. As soon as the flyback current iF reaches zero, the voltage VT drops below the battery voltage VBAT. Hence, using the comparator 166, which compares VT to VBAT, a determination is easily made as to when the flyback current, which represents the transformer current and which also transfers energy to the output capacitors as long as it is non-zero, has gone to zero.

In accordance with the present invention, as soon as the transformer current reaches the programmed peak value, the switch Q1 is turned off, and the transformer current thereafter ramps back to zero. Energy is transferred to the output capacitor 56 as long as current is flowing in the primary winding of the transformer, whether such current is iT or iF. As soon as the transformer current reaches zero, which signifies the cessation of delivery of energy to the output capacitor, the oscillator is enabled so as to again turn the switch Q1 on, thereby starting the process over again. In this manner, there is very little dead time during which energy is not being transferred to the output capacitor 56, thereby reducing the time to charge the output capacitors.

As is evident from FIG. 6, by adjusting the programmable peak current reference value, ipk, it is possible to adjust the ON and OFF time of the oscillator so as to control the amount of energy transferred through the transformer T1 during each oscillator cycle. The oscillator 160 (which, as is evident from the above description, is not a free-running oscillator; but rather is a slave oscillator that produces a high output until the peak current is reached, whereupon it produces a low output until enabled by sensing that the transformer current has reached zero) preferably operates at a frequency above the audible range of humans, e.g., 25–50 kHz.

Returning to FIG. 5, it is seen that the control signals for controlling the switches S1–S5, labeled S1C–S5C, are all generated as controlled by the control/timing circuit 22. A transformer T4, for example, produces the control signal S5C for controlling the switch S5 at a secondary winding in response to a suitable control signal, S-5, applied to the primary winding of the transformer T4. The control signal S-5 is generated by the control/timing circuit 22 Advantageously, the control signals S1C and S4C are generated simultaneously by applying a single control signal S-¼ to the primary winding of a transformer T2. Similarly, the control signals S2C and S3C are generated simultaneously by applying a single control signal S-⅔ to the primary winding of a transformer T3. Both the transformers T2 and T3 have two secondary windings, with one secondary winding controlling one switch, and the other secondary winding controlling the other switch. In this manner, only the appropriate switches on opposite sides of the "H" configuration of the switch network 58 can be turned on at one time, as is required to deliver the high voltage pulse to the heart in accordance with a desired polarity, and such result is achieved by using a single control signal, without any additional logic or control required.

As described above, it is thus seen that the present invention provides a tiered therapy ICD that advantageously affords a reduced time-to-therapy, thereby reducing the exposure of the patient to a tachyarrhythmia and increasing the probability of a successful cardioversion-defibrillation attempt.

It is also seen from the above description that the reduced time-to-therapy is provided by charging the high voltage output capacitors during the application of a less aggressive therapy, or while attempting to verify if a prior therapy attempt was successful, thereby allowing such capacitors to be fully charged and ready in the event a more aggressive therapy is needed.

As further described above, it is seen that the invention provides a charging circuit for charging one or more high voltage output capacitors within a tiered therapy ICD device, which charging circuit advantageously minimizes the time period required to obtain a prescribed charge on the high voltage output capacitors.

While the invention herein disclosed has been described by means of specific embodiments and applications thereof, numerous modifications and variations could be made thereto by those skilled in the art without departing from the scope of the invention set forth in the claims.

What is claimed is:

1. An implantable cardioverter-defibrillator (ICD) comprising:
    a sensing circuit that senses electrogram (EGM) signals through a sensing lead adapted to be coupled to a patient's heart;
    control logic and timing circuits that determine whether the EGM signals sensed by the sensing circuit is indicative of a tachyarrhythmia;
    a pulse generator that selectively generates stimulation pulses of a first energy in a prescribed pattern as controlled by the control logic and timing circuits, the stimulation pulse of the first energy being applied to the patient's heart through the sensing lead in an attempt to terminate the sensed tachyarrhythmia;
    a shocking electrode system adapted to be coupled to the patient's heart; and
    a cardioversion-defibrillation circuit that selectively generates stimulation pulses of a second energy as controlled by the control logic and timing circuits, the stimulation pulse of the second energy being applied to the patient's heart through the shocking electrode system in an attempt to terminate the sensed tachyarrhythmia, said cardioversion-defibrillation circuit including a high voltage output capacitor, a charging circuit that charges the high voltage output capacitor to a specified charge energy as controlled by the control logic and timing circuits, and a switching circuit that selectively connects the high voltage output capacitor to the shocking electrode system as controlled by the control logic and timing circuits in order to generate the stimulation pulses of said second energy;

the control logic and timing circuits including means for terminating the sensed tachyarrhythmia in accordance with a tiered therapy, the tiered therapy including a first tier that applies the stimulation pulses of the first energy in response to sensing a given tachyarrhythmia, and a second tier that applies the stimulation pulses of the second energy immediately after determining that the first tier could not successfully terminate the tachyarrhythmia, and early charging means for controlling the charging circuit so that it charges the high voltage output capacitor to the specified charge energy before concluding the first tier of the tiered therapy;

whereby in the event the first tiered therapy does not terminate the tachyarrhythmia, the second tier of therapy may be immediately applied without having to wait for the high voltage output capacitor to be charged.

2. The ICD as set forth in claim 1 wherein the cardioversion-defibrillation circuit further selectively generates stimulation pulses of a third energy as controlled by the control logic and timing circuits, said stimulation pulse of said third energy also being applied to the patient's heart through the shocking electrode system, and wherein the tiered therapy further includes a third tier that applies the stimulation pulses of the third energy immediately after determining that the second tier could not successfully terminate the tachyarrhythmia, and wherein the early charging means begins to charge the high voltage output capacitor before the conclusion of the second tier of the tiered therapy.

3. The ICD as set forth in claim 1 wherein the first tier of the tiered therapy includes a therapy phase and a verification phase, and wherein the early charging means controls the charging circuit to charge the high voltage output capacitor during the therapy phase of the first tier of the tiered therapy; whereby the second tier may be immediately applied as soon as a determination is made that the first tier was unsuccessful without having to wait for the high voltage output capacitor to be charged to the specified charge energy by the charging circuit.

4. The ICD, as set forth in claim 3, wherein the tiered therapy invoked by the control logic and timing circuits further includes a third tier that applies stimulation pulses of a third energy to the patient's heart through the shocking electrode system after determining that the second tier could not successfully terminate the tachyarrhythmia.

5. The ICD, as set forth in claim 4, wherein the control logic and timing circuits cause the charging circuit to charge the high voltage output capacitor to a selected one of two prescribed charge energies;
a first of the prescribed charge energies corresponding to the second tier of the tiered therapy; and
a second of the prescribed charge energies corresponding to the third tier of the tiered therapy;

the control logic and timing circuits being configured to cause the charging circuit to charge the high voltage output capacitor to the second prescribed charge energy during the application of the second tier of the tiered therapy;

whereby the third tier may be applied as soon as a determination is made that the second tier was unsuccessful without having to wait for the high voltage output capacitor to be charged to the second prescribed charge energy by the charging circuit.

6. The ICD as set forth in claim 1 wherein the first tier of the tiered therapy includes a therapy phase and a verification phase, and wherein the early charging means controls the charging circuit to charge the high voltage output capacitor during the verification phase of the first tier, said verification phase beginning at a time during which the EGM signals following the therapy phase of the first tier of the tiered therapy are being analyzed to determine if the first tier was successful in terminating the tachyarrhythmia; whereby the second tier may be applied as soon as a determination is made that the first tier was unsuccessful without having to wait for the high voltage output capacitor to be charged to the specified charge energy by the charging circuit.

7. The ICD, as set forth in claim 6, wherein the tiered therapy invoked by the control logic and timing circuits further includes a third tier that applies stimulation pulses of a third energy to the patient's heart through the shocking electrode system after determining that the second tier could not successfully terminate the tachyarrhythmia.

8. The ICD, as set forth in claim 7, wherein the control logic and timing circuits cause the charging circuit to charge the high voltage output capacitor to a selected one of two prescribed charge energies;
a first of the prescribed charge energies corresponding to the second tier of the tiered therapy; and
a second of the prescribed charge energies corresponding to the third tier of the tiered therapy;
the control logic and timing circuits being configured to cause the charging circuit to charge the high voltage output capacitor to the second prescribed charge energy beginning at a time during which the EGM signals following application of the second tier of the tiered therapy are being analyzed to determine if the second tier was successful in terminating the tachyarrhythmia;

whereby the third tier may be applied as soon as a determination is made that the second tier was unsuccessful without having to wait for the high voltage output capacitor to be charged to the second prescribed charge energy by the charging circuit.

9. An implantable cardioverter-defibrillator (ICD) comprising:
sensing and logic circuits to sense a tachyarrhythmia through one or more sensing and shocking electrodes adapted to be coupled to a patient's heart;
low and high voltage output capacitors coupled to the sensing and shocking electrodes, respectively, through an output switch;
a charging circuit that charges the output capacitors to a specified energy; and
a control circuit that generates control signals, the control signals being coupled to the charging circuit and output switch for controlling the charging of the low and high voltage output capacitors and the closure of the output switch in accordance with a prescribed tiered therapy, the tiered therapy including a therapy phase during which a less aggressive therapy is applied through at least one of the sensing or shocking electrodes, followed by a verification phase to determine if the less aggressive therapy was successful in terminating a sensed tachyarrhythmia, followed by a more aggressive therapy applied through at least one of the sensing or shocking electrodes in the event the less aggressive therapy was not successful in terminating the sensed tachyarrhythmia; the control circuit further including reduced time-to-therapy means for charging the high voltage output capacitors to a prescribed energy at the same time as a specified one of the therapy phase or the verification phase is being carried out in accordance with the prescribed tiered therapy;

whereby the ICD automatically uses the least aggressive therapy of the prescribed tiered therapy as it attempts to terminate tachyarrhythmias, and in doing so employs an early charging feature to reduce the time to therapy.

10. The implantable ICD, as set forth in claim 9, wherein the reduced time-to-therapy means charges the high voltage output capacitors to the prescribed energy at the same time as the therapy phase of a prior less aggressive therapy.

11. The implantable ICD, as set forth in claim 9, wherein the reduced time-to-therapy means charges the high voltage output capacitors to the prescribed energy at the same time as the verification phase of a prior less aggressive therapy.

12. The implantable ICD, as set forth in claim 11, wherein the prescribed tiered therapy includes three different therapies, a first therapy comprising the application of low energy stimulation pulses, a second therapy comprising the application of a moderate energy stimulation pulse, and a third therapy comprising the application of a high energy stimulation pulse; the first therapy being a less aggressive therapy than either the second or third therapy; the second therapy being a less aggressive therapy than the third therapy, but a more aggressive therapy than the first therapy; and the third therapy being a more aggressive therapy than either the first or second therapy.

13. The implantable ICD, as set forth in claim 12, wherein the specified energy to which the output capacitors are charged in accordance with the second therapy comprises 1 to 10 joules.

14. The implantable ICD, as set forth in claim 12, wherein the specified energy to which the output capacitors are charged in accordance with the third therapy comprises 11 to 40 joules.

15. The implantable ICD, as set forth in claim 12, wherein the low energy stimulation pulses are applied in a prescribed sequence that includes a selected one of ramp pacing, burst pacing, or scanning pacing.

16. The implantable ICD, as set forth in claim 12, wherein the low voltage output capacitors are used in providing the first therapy, and the high voltage output capacitors are used in providing the second and third therapies.

17. The implantable ICD, as set forth in claim 9, wherein the charging circuit includes:

a transformer that couples a primary power source to the high voltage output capacitor as controlled by control signals generated by the control circuit, the control signals creating an ON time during which a primary winding of the transformer is connected to the primary power source, and an OFF time during which the primary winding is disconnected from the primary power source; and current sensing means for sensing the charging current flowing through the transformer and for controlling the duration of the ON and OFF times as a function of the charging current thus sensed.

18. The implantable ICD, as set forth in claim 17, wherein the current sensing means senses when the charging current during the ON time reaches a prescribed peak value, and wherein the control circuit terminates the ON time as soon as the charging current reaches the prescribed peak value, the prescribed peak value being selected so as to charge the high voltage output capacitor to the specified energy in prescribed increments.

19. The implantable ICD, as set forth in claim 18, wherein the current sensing means senses when the charging current during the OFF time has decayed to a prescribed minimum value, and wherein the control circuit terminates the OFF time as soon as the charging current reaches the prescribed minimum value; whereby the duration of the OFF time is minimized.

20. The implantable ICD, as set forth in claim 19, wherein the prescribed minimum value is zero.

21. A method of operating an implantable cardioverter-defibrillator (ICD), the ICD having output means for delivering an electrical shock of a prescribed energy to the heart of a patient, and means for sensing a tachyarrhythmia of the patient's heart; the method comprising the steps of:

(a) sensing a tachyarrhythmia;

(b) issuing a first therapy comprising an electrical shock of a first energy in an attempt to terminate the sensed tachyarrhythmia;

(c) checking to see if the first therapy was successful in terminating the tachyarrhythmia;

(d) charging a high voltage output capacitor of the ICD to a specified charge level in anticipation of applying a second therapy comprising an electrical shock of a second energy, the second energy being greater than the first energy, the charging of the high voltage output capacitor for application of the second therapy being commenced simultaneously with the checking of step (c); and (e) issuing the second therapy as soon as the charging of step (d) has been completed, and as soon as a determination has been made in step (c) that the first therapy was not successful.

22. The method, as set forth in claim 21, further including:

(f) checking to see if the second therapy was successful in terminating the tachyarrhythmia;

(g) charging the high voltage output capacitor of the ICD to a different specified charge level in anticipation of applying a third therapy comprising an electrical shock of a third energy, the third energy being greater than the second energy, the charging of the high voltage output capacitor for application of the third therapy being commenced simultaneously with the checking of step (f); and (h) issuing the third therapy as soon as the charging of step (g) has been completed, and as soon as a determination has been made in step (f) that the second therapy was not successful.

23. The method, as set forth in claim 22, wherein the second energy comprises 5 to 10 joules, and the third energy comprises 11 to 40 joules.

24. The method, as set forth in claim 21, further including repeating steps (b) to (d) a prescribed number of times before commencing step (e).

25. The method, as set forth in claim 24, wherein the prescribed number of times that steps (b) to (d) are repeated before commencing step (e) comprises at least two times.

* * * * *